United States Patent
Greenberg et al.

(10) Patent No.: US 8,690,810 B2
(45) Date of Patent: Apr. 8, 2014

(54) METHOD AND DEVICES FOR PREVENTING OR MINIMIZING RECURRENT ELBOW TENDINOSIS

(75) Inventors: Mark H. Greenberg, Jensen Beach, FL (US); Aldo Burga, Port St. Lucie, FL (US)

(73) Assignee: TendonEase, LLC, Palm City, FL (US)

( * ) Notice: Subject to any disclaimer, the term of this patent is extended or adjusted under 35 U.S.C. 154(b) by 117 days.

(21) Appl. No.: 13/106,484

(22) Filed: May 12, 2011

(65) Prior Publication Data

US 2012/0095378 A1 Apr. 19, 2012

Related U.S. Application Data

(60) Provisional application No. 61/334,046, filed on May 12, 2010.

(51) Int. Cl.
*A61F 5/00* (2006.01)
(52) U.S. Cl.
USPC ............................................ 602/22; 128/880
(58) Field of Classification Search
USPC ........................ 602/22; 128/880; 482/44, 88
See application file for complete search history.

(56) References Cited

U.S. PATENT DOCUMENTS

| | | | | |
|---|---|---|---|---|
| 5,062,623 A | * | 11/1991 | Smith et al. | 271/283 |
| 5,214,799 A | * | 6/1993 | Fabry | 2/161.6 |
| 5,762,621 A | * | 6/1998 | Schultz | 602/64 |
| 2004/0019308 A1 | | 1/2004 | Chow | |
| 2007/0021700 A1 | | 1/2007 | Liebowitz | |
| 2007/0276304 A1 | | 11/2007 | Greenberg et al. | |

FOREIGN PATENT DOCUMENTS

FR 2892298 A1 4/2007

OTHER PUBLICATIONS

International Search Report and Written Opinion issued in PCT/US2011/036260, mailed Oct. 7, 2011, 12 pages.

* cited by examiner

*Primary Examiner* — Patricia Bianco
*Assistant Examiner* — Camtu Nguyen
(74) *Attorney, Agent, or Firm* — Davis, Brown, Koehn, Shors & Roberts, P.C.

(57) ABSTRACT

Methods of preventing the development or exacerbation of tendinosis include receiving a first ring of resilient material over a first digit of a hand of the user and a second ring of resilient material over a second digit of the hand of the user. The first and second digits receiving first and second rings are curled about an object to grasp the object with an increased circumference grip relative to a natural grip of the user. The first and second rings are automatically slid to an interleaved configuration on the first and second digits by moving the grasped object with the hand.

12 Claims, 2 Drawing Sheets

METHOD AND DEVICES FOR PREVENTING OR MINIMIZING RECURRENT ELBOW TENDINOSIS

CROSS-REFERENCE TO RELATED APPLICATIONS

This application claims the benefit of U.S. Provisional Application 61/334,046, filed May 12, 2010 and entitled "Method and Devices for Preventing or Minimizing Recurrent Elbow Tendinosis," which is hereby incorporated herein by reference in its entirety.

TECHNICAL FIELD

The embodiments disclosed herein relate to methods and devices for preventing or minimizing recurrent elbow tendinitis. Exemplary embodiments include methods and devices relating to two or more rings positioned on two or more of the user's fingers in specific configurations as described herein.

BACKGROUND

Elbow tendinosis is often described as "tennis elbow" when referring to the lateral elbow or "golfer's elbow" when referring to the medial elbow. Elbow tendinosis is typically due to repetitive trauma to the tendon at the insertion at the elbow. The tendon develops microscopic tears and subsequent degenerative change. There is typically no true inflammation, however, and therefore, elbow tendinosis is distinguishable from a true "tendonitis." Athletic activities such as golf and tennis, as well as other repetitive activities, such as using a hammer, often are the cause of tendinosis.

Some devices for mitigating elbow tendinosis have included braces near the elbow insertion of the tendon. These braces press the tendon into the underlying muscle mass and have included different features, such as gel padding or air bladders for this purpose. Some problems with these types of braces include the necessity for precise placement, the need for readjustment during use as the forearm muscle enlarges with activity, and the discomfort of having a constricting tourniquet-like band around the forearm.

SUMMARY

Some aspects of inventive embodiments relate to a tendinosis system for helping prevent the development of and/or recurrence of elbow tendinosis. The system includes a first pad made of a resilient material and configured for being carried by a first digit of a user of the system. The first pad is substantially tubular and has an inner diameter adapted to allow rotation about and axial sliding along a phalanges of the first digit during grasping with the first digit without passing an interphalangeal joint of the first digit. The second pad is also made of a resilient material and configured for being carried by a second digit of the user that is adjacent to the first digit of the user. The second pad is substantially tubular and has an inner diameter adapted to allow rotation about and axial sliding along a phalanges of the second digit during grasping with the second digit without passing an interphalangeal joint of the second digit. The first and second pads are adapted to slide axially along the phalanges of the first and second digits, respectively, to an interleaved configuration during use.

Other aspects of inventive embodiments relate to a method of preventing the development or exacerbation of tendinosis. The method includes receiving a first ring of resilient material over a first digit of a hand of the user and a second ring of resilient material over a second digit of the hand of the user. The first and second digits receiving first and second rings are curled about an object to grasp the object with an increased circumference grip relative to a natural grip of the user. The method also includes automatically sliding the first and second rings to an interleaved configuration on the first and second digits by moving the grasped object with the hand.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
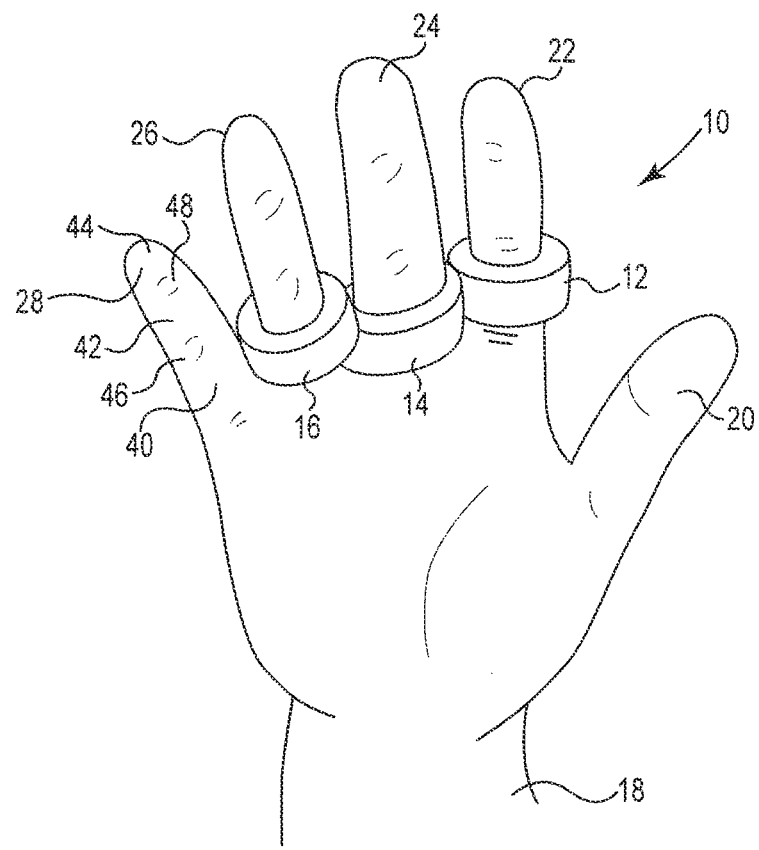
FIG. 1 is a perspective view of a tendinosis system located on a hand of a user, according to some embodiments.

While the various embodiments disclosed herein are amenable to various modifications, permutations, and alternative forms, specific embodiments have been shown by way of example in the drawings and are described in detail below. The intention, however, is not to limit the invention to the particular embodiments described. On the contrary, the various embodiments are intended to cover all modifications, equivalents, and alternatives falling within the scope of the invention or inventions as defined by the appended claims.

DETAILED DESCRIPTION

Various aspects disclosed herein relate to protecting against reinjuring a torn tendon once the tendon has healed and a participant re-engages in the physical activity that originally caused or worsened the tendinosis.

Some embodiments relate to a preventative and therapeutic system adapted to be worn on a user's hand, the system including a plurality of rings adapted to move rotationally and/or axially along the user's fingers during use. In other embodiments, the rings have a shape and minimal thickness that result in a less acute metacarpalphalangeal joint angle. The system is optionally used to prevent and/or mitigate the effects of recurrent elbow tendinosis, where the term "recurrent" delineates a usefulness in letting a person re-engage in the specific activity that at first caused elbow tendon injury and the term "tendinosis" is a true delineation of pathology at the medial or lateral elbow epicondyle (in comparison to tendonitis, which indicates inflammation). The dynamic nature of the system promotes therapeutic efficacy as well as user comfort. In some embodiments, the rings automatically interact with one another during use to create an interleaving pattern on the user's fingers, thereby enhancing comfort for the user.

In some embodiments, the system includes a plurality of tubular rings, each ring having a rounded end such that rings worn on adjacent fingers move against one another to integrate together, moving naturally to a comfortable position for the user during use, such as, in some exemplary embodiments, an interleaved configuration as described in further detail below, which minimizes finger splay and/or other uncomfortable hand positioning. The rings are optionally formed of visco-elastic polymer, such as material sold under the tradename, "SORBOTHANE," available from Sorbothane, Inc. of Kent, Ohio, although other materials are contemplated. In some related embodiments, one or more of the rings are adapted to help reduce and/or prevent substantial bending of the proximal interphalangeal joint (PIPJ), which helps decrease tendon tension during use.

FIG. 1 shows a tendinosis system 10 for helping prevent the development of and/or recurrence of elbow tendinosis, according to some embodiments. As shown, the system 10 includes a plurality of pads, such as a first pad 12, a second pad 14, and a third pad 16, each of which is worn by a user 18. The pads 12, 14 and 16 help reduce grip tightness by the user 18 when grasping an object during an activity (e.g., the handle of a tennis racket or a golf club) so that less of the impact forces applied to the object (a tennis ball strike) are transferred through the tendon-muscle-tendon unit of the user 18. The pads 12, 14 and 16 are also made of a resilient material and sized so as to absorb impact forces applied to the object to further reduce resultant impact stress. The system 10 may be arranged in a variety of manners in accordance with various embodiments.

As shown in FIG. 1, the hand of the user 18 has a thumb 20, an index finger 22, a middle finger 24, a ring finger 26, and a little finger 28. The fingers 22, 24, 26 and 28 each includes a proximal phalange 40 that is adjacent the palm of the user 18, a proximal interphalangeal joint 46 located intermediate the proximal phalange 40 and a middle phalange 42, and a distal interphalangeal joint 48 located intermediate the middle phalange 42 and a distal phalange 44. Other than a middle phalange 42 and a distal interphalangeal joint 48, the thumb 20 includes similar structures.

As shown, the pads 12, 14 and 16 are generally configured as rings that extend completely around the fingers 22, 24 and 26, respectively. In some embodiments, the pads 12, 14 and 16, also described as rings, are substantially similar in shape, and thus are described collectively with respect to the first pad 12. In some embodiments, the pads 12, 14 and 16 are of differing sizes and in other embodiments the pads 12, 14 and 16 are of substantially the same shape, size, and material as desired.

Figure 2:
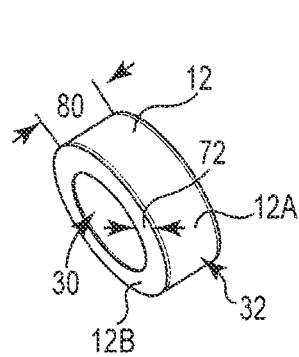
FIG. 2 is a perspective view of a first pad of the system of FIG. 1, according to some embodiments.
Figure 3:
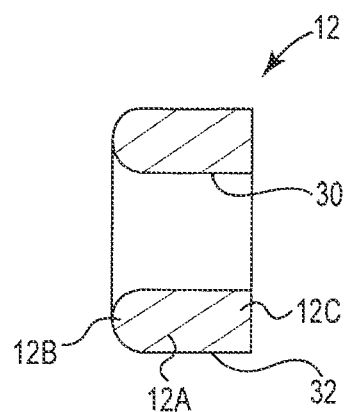
FIG. 3 shows a longitudinal section of the first pad of FIG. 2, according to some embodiments.

FIG. 2 is a perspective view of the first pad 12 and FIG. 3 is a longitudinal section of the first pad 12, according to some embodiments. As shown, the first pad 12 has a palmar side 30 that is configured for contacting the finger 22 of the user 18 and an oppositely disposed dorsal side 32. Generally, the first pad 12 is substantially tubular, or ring-like, which helps avoid loss of contact even if the pad twists or twirls around the finger 22 during use. The first pad 12 may be a single, integral piece or may be made of one or more components.

Generally, the first pad 12 has sufficient firmness to elevate the proximal phalange 40 from a held object that is being impacted by the held object. By elevating the proximal phalange 40, tension in the tendon-muscle-tendon unit is loosened, thereby causing less kinetic energy to be imparted to the elbow at a time of impact. In some embodiments, first pad 12 has a firmness as measured on the Shore Durometer 00 scale between approximately 55 and approximately 70, although other degrees of firmness are contemplated. In some embodiments, the first pad 12 is made of a soft, shock absorbent material, such as SORBOTHANE. Other materials that may be used to construct the first pad 12 include polyurethane, gel, silicone or foam, for example. In another embodiment, the material can be any material that is elastic or finitely compressible. The first pad 12 may also have absorbent properties that act to remove perspiration from the skin of the user 18 during use of the system 10.

As shown in FIGS. 2 and 3, the first pad 12 defines a main body 12A, a first end 12B, and a second end 12C. The main body 12A is substantially tubular and has a substantially uniform thickness 72 about its axis, according to some embodiments. The first end 12B is substantially rounded and the second end 12C is substantially flat, although a rounded second end 12C is contemplated.

As shown, the main portion 12A of the first pad 12 has a uniform thickness between the inner and outer circumferences of the pad 12 and therefore has substantially no projections on any particular surface. The inner circumference varies based upon the finger size of the user but is generally slightly greater than a circumference of the finger 22, and in particular the proximal phalange 40, to help allow the first pad 12 to freely rotate in either direction as well as help allow the first pad 12 to move up and down, or axially, along the finger 22. The first pad 12 has a thickness 72 of at least six millimeters, according to some embodiments. For example, the thickness 72 is optionally approximately nine millimeters, although other dimensions are contemplated. In a further alternative example, the thickness 72 is optionally at least 10 millimeters. Although described as having a constant thickness 72, it is to be understood that the thickness 72 may be varied in other embodiments. According to certain implementations, the minimal thickness is any minimal thickness that results in a less acute metacarpalphalangeal joint angle of the fingers of the user while gripping the handle of any object contemplated in this application. In accordance with some embodiments, the first pad 12 has a length 80 from approximately ten millimeters to approximately thirteen millimeters, although other dimensions are contemplated.

As shown, the first, second, and third pads 12, 14 and 16 are retained on the proximal phalanges 40 of the index finger 22, the middle finger 24, and the ring finger 26, respectively. The pads 12, 14 and 16 are shown interleaved, or integrated, in such a manner that each of the pads 12, 14, 16 is able to contact the two fingers adjacent the finger on which the particular one of the pads 12, 14 and 16 is received. As described in greater detail, the pads 12, 14, 16 are configured to naturally encourage this type of configuration during use, automatically sliding into a more compact arrangement (e.g., in comparison to the pads being aligned, one next to the other, which otherwise increases finger splay and user discomfort).

Though the pads 12, 14 and 16 are shown on the proximal phalanges 40, in various embodiments the pads 12, 14 and 16 are adapted to slide axially along the finger on which they are received to an axial location on that finger (e.g., on the middle phalange 42) that is comfortable to the user and also maintains an interleaved configuration. Additionally, though a single pad is shown on a respective finger, in other embodiments multiple pads are received on one or more fingers, those pads also naturally sliding to a comfortable, interleaved position during use. For example, selection and location of the pads may be made based upon a particular form of tendinosis affecting the user 18. When the user 18 is experiencing a form of tendinosis commonly known as tennis elbow, a pad may be located on the middle finger 24. When the user 18 experiences a form of tendinosis commonly referred to as golfer's elbow, multiple pads may be located on the index finger 22 and the ring finger 26. If the user 18 experiences both of these forms of tendinosis, multiple pads may be placed on the index, middle and ring fingers 22, 24, and 26, for example. Additionally, though not shown, one or more pads are optionally placed on the thumb and/or little finger 20, 28, respectively. In certain alternative configurations of the system, pads are placed on the user's specific fingers related to the tendinosis while simultaneously allowing remaining fingers to exert enough pressure for the user to maintain a grip on various objects. As such, various combinations and numbers of pads are envisioned as making up the system 10 in accordance with various embodiments.

Additional and/or alternate systems (e.g., elbow braces) are optionally employed in conjunction with the system 10. For example, U.S. Patent Application Publication 2007/0276304, "Apparatus for preventing or minimizing tendinitis" describes various useful apparatuses and methods for preventing the development or exacerbation of tendinitis that are usable with the system 10, the contents of that publication being incorporated herein by reference in its entirety.

Figure 4:
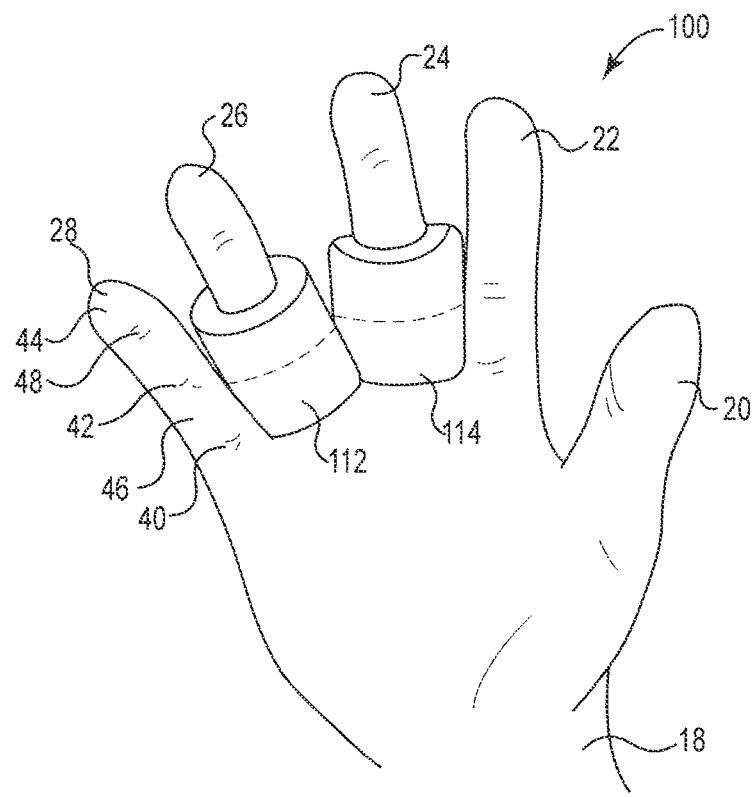
FIG. 4 shows another tendinosis system located on the hand of the user, according to some embodiments.

FIG. 4 is a perspective view of another tendinosis system 100 for helping prevent the development of and/or recurrence of elbow tendinosis, according to some embodiments. As shown, the system 100 includes a plurality of pads, such as a first pad 112 and a second pad 114, each of which is worn by the user 18. The pads 112 and 114 help reduce grip tightness by the user 18 similarly to the system 10. The pads 112 and 114 are also made of a resilient material and sized so as to absorb impact forces applied to the object to further reduce resultant impact stress. The system 100 may be arranged in a variety of manners in accordance with various embodiments.

As shown, the pads 112 and 114 are generally configured as rings that extend completely around the fingers 26 and 24, respectively. In some embodiments, the pads 112 and 114, also described as rings, are substantially similar, and thus are described collectively with respect to the first pad 112.

Figure 5:
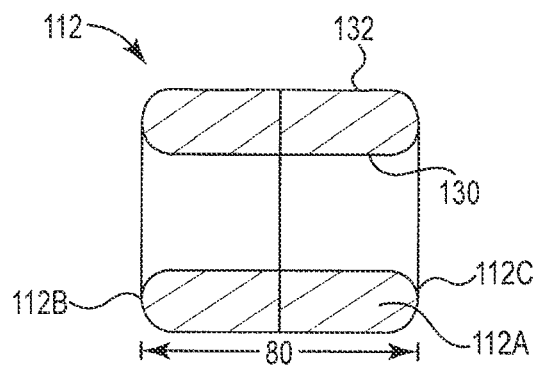
FIG. 5 is a longitudinal section of a first pad of the system of FIG. 4, according to some embodiments.

FIG. 5 is a longitudinal section of the first ring 112, according to some embodiments. The first ring 112 has a palmar side 130 that is configured for contacting the finger 22 of the user 18 and an oppositely disposed dorsal side 132. Generally, the first pad 112 is substantially tubular, or ring-like, which helps avoid loss of contact even if the pad twists or twirls around the finger 22 during use. The first pad 112 may be a single, integrally molded piece or may be made of one or more components (e.g., of two substantially smaller pads, such as the pad 12, pressed or joined together).

Generally, the first pad 112 is optionally formed of similar materials and/or using similar methods (e.g., molding) to that of the first pad 12. The first pad 12 has sufficient firmness to elevate the proximal phalange 40 from a held object that is being impacted by the held object to loosen the tension in the tendon-muscle-tendon unit to the elbow.

Though of substantially similar thickness and having a substantially similar inner and outer circumferences to the first pad 12, the first pad 112 is generally more elongated than the first pad 12, e.g., having a length 80 of approximately twenty-six millimeters or more, although other dimensions are contemplated. The more elongate form of the first pad 112 is configured to more directly impede, while not precluding, flexion of the proximal interphalangeal joint 46 to further decrease the tension of the finger tendon(s) involved in elbow tendinosis. Though the first pad 112 is able to rotate about the finger on which the first pad 112 is received, axial, or linear movement of the pad 112 on the finger is impeded (e.g., by the bent or flexed interphalangeal joint 46) while grasping an object.

As shown in FIG. 5, the first pad 112 defines a main body 112A, a first end 112B, and a second end 112C. The main body 112A is substantially tubular and has a substantially uniform thickness 172 about its axis, according to some embodiments. The first and second ends 112B, 112C are substantially rounded for comfort, for example.

As shown, the first and second pads 112 and 114 are retained over the proximal interphalangeal joints 46 of the middle finger 24 and the ring finger 26, respectively. The pads 112 and 114 are not shown interleaved, or integrated, due to their increased lengths.

Though the pads 112 and 114 are shown together, in various embodiments one or more of the pads 112 and 114 are replaced by pads similar to the pads 12, 14 and 16. For example, in some embodiments, the index finger 22 receives the pad 112 while the middle and ring fingers 24, 26 receive pads similar to pads 14 and 16, which permits interleaving between the pads on the middle and ring fingers 24, 26 to reduce finger splay while substantially inhibiting bending of the proximal interphalangeal joint 46 of the index finger 22. As such, various other combinations and numbers of pads are envisioned as making up the system 100 in accordance with various embodiments.

Some methods of reducing tendinosis risk, for example preventing the development or exacerbation of tendinosis, include receiving the pads 12, 14, 16 on the proximal phalanges 40 of the fingers 22, 24 and 26, respectively, and grasping an object by bending the fingers 20, 22, 24, 26 and 28 about the object. For example, prior to engaging in an activity known to aggravate elbow tendinosis, the user places the system 10 on the target finger(s) (e.g., those corresponding to tendons having caused or tending to cause tendinosis for the user) as one would place a ring on a finger. The user 18 optionally determines which specific finger tendon(s) transmits the kinetic energy producing the most damage to the elbow by simply moving each finger up and down while placing the opposite hand on the previously injured area of the elbow. If finger movement produces some tenderness at the elbow, then that finger (or fingers) should have one or more of the pads of the system 10 placed upon it. The user then verifies that the inner circumference of the pad(s) allow the device to move freely in rotational and translational directions (e.g., about and along the proximal phalanges 40). The user also optionally confirms that the pad(s) are not so loose upon the finger that the pad moves undesirably, for example that the particular pad does not move distal to the proximal interphalangeal joint 46 while gripping the hitting implement.

Without being limited by theory, it is believed that certain embodiments disclosed herein mitigate elbow tendinosis by reducing tendon tension near the elbow when worn. Conceptually, in terms of transmission of energy along the tendons of the user 18 from the hand to the elbow, kinetic energy is proportional to velocity squared, or the speed of the vibrations through the tendon, and wave velocity squared is directly proportional to tendon tension. Therefore, kinetic energy transmitted along a string apparatus (i.e., the tendons) is directly proportional to the tension of that string. The pads, worn as rings, help prevent maximal flexion of the fingers, and resultant tightening of the tendons (the "strings"). The pads decrease the tension of the finger tendons by keeping a finger segment away from the object being gripped during use, and particularly at the moment of impact. In some embodiments, the tendon insertion on the elbow thus experiences greatly reduced impact (relative to scenarios where the system 10 is not in use), which in most cases is below a threshold for reinjuring the tendon at the elbow insertion. Moreover, the user 18 is still allowed to grip the object tightly, such as by placing the pads on only selected fingers according to certain embodiments, without over tensioning the tendons in the fingers.

As alluded to above, the pads 12, 14 and 16, function to keep the index finger 22, middle finger 24, and ring finger 26 from directly touching a gripping surface to reduce tension in the users fingers while grasping the object. In some embodiments, one or more of the pads 12, 14 and 16 help keep one or more of the fingers 22, 24 and/or 26 from bending as much as it normally would in gripping the object. Thus, methods include using the system 10 to create laxity in the connection between the tendon of the finger, the muscle of the forearm pulling on the tendon of the finger, and the tendon in the elbow attached to the muscle of the forearm. By preventing the finger(s) 22, 24 and/or 26 from bending to the same extent they normally would when grasping the object, the aforementioned tendon-muscle-tendon unit is not completely tight and enjoys some degree of looseness. Use of the system 10 thus increases an effective grip circumference of the fingers 22, 24 and 26. In some embodiments, the pads 12, 14 and 16 do not interfere with the bending of the interphalangeal 46 and 48 or metacarpalphalangeal joints of the hand of the user 18 yet engage the fingers in a manner so as to be precluded from twisting or slipping off the finger 24 or out of position.

In particular, impact forces on the object being held by the hand of the user 18 are transferred through the finger 24 and the tendon-muscle-tendon unit. These forces act to cause tendinosis and are more quickly and strongly propagated if the tendon-muscle-tendon unit is tight (e.g., much the same way a wave is more strongly and quickly propagated along a tighter rather than looser wire). As the system 10 causes the tendon-muscle-tendon unit to be looser than normal, impact forces generated from the object being held are of a lower magnitude and speed through the tendon-muscle-tendon unit. As such, the resulting pull forces on the elbow of the user 18 are reduced thus preventing or reducing tendinosis. The system 10 thus acts to decrease the strength of the shock wave imparted and slows the propagation of the diminished shock wave so that it dissipates and exerts decreased pull upon the tendon at the elbow.

Additionally, as the tendon-muscle-tendon unit has a degree of laxity imparted thereto, there is little chance of exceeding the tensile strength of the tendon even if a higher impact than usual is transmitted to the object being gripped such as when an off-center or high velocity shot is hit while playing tennis. Also, as the pads 12, 14 and 16 have relatively large thicknesses and are made of a resilient shock absorbing material, they further act to dampen impact forces imparted onto the object being grasped. Here, the pads 12, 14 and 16 directly absorb some of the kinetic energy transmitted from the object (not shown) at the grip interface and, hence, reduce the kinetic energy transmitted to the tendon at the blow.

Moreover, correctly configured, the pads 12, 14 and 16 naturally move in an axial position on the fingers (e.g., on the proximal phalanges 40) to an interleaved configuration such as that shown in FIG. 1. In particular, as the user grasps the object being held and swings the object, the gripping force of the hand and the ability of the pads 12, 14 and 16 to slide axially on the fingers 22, 24 and 26 causes the pads 12, 14 and 16 to naturally move to a more comfortable, interleaved configuration. And, if the user desires to enhance comfort manually, the user simply slides the pads 12, 14 and 16 to various positions until the pads retain a desirable position or move naturally to a desired position on the fingers. Although periodic adjustment is contemplated, continued use of the gripped object (e.g., playing tennis) generally will not cause the system 10 to lose any amount of resiliency and, as such, the system 10 generally does not need to be readjusted or tightened during use, according to some embodiments.

As referenced above, the systems 10, 100 may be used in conjunction with other types of elbow braces and pads in addition to being used with specially designed grips. Although described as being used in relation to golf and tennis, the systems 10, 100 may be used in relation to any activity in which a user 18 grasps an object. For example, the systems 10, 100 can be used in relation to hockey sticks, baseball bats, softball bats, fishing poles, ropes for rope climbing, wind surfing handles, rowing handles, bicycle handles and snowmobile handles. Further activities in which the systems 10, 100 may be used include housecleaning, the use of hand tools, use of a chainsaw, lawnmower and garden tool use, use of musical instruments, wheel barrow use, crane operation, window washing, holding of retractors during surgery, plumbing work, hair dryer use, exercise equipment use, handicap fall bar use, wheelchair use, physical therapy equipment use, painting and truck loading. The systems 10, 100 can be used in any application that involves repetitive motion or shock to the hand of the user 18.

In accordance with the foregoing, the systems 10 and/or 100 incorporate a variety of features. For example, the system 10 includes one or more pads in ring form configured to rotate around the finger on which they are worn as well as move up and down the finger segment on which they are worn. When a plurality of rings are used, the system 10 is substantially more comfortable as the pads (e.g., pads 12, 14 and/or 16) automatically move with object being grasped to a comfortable and effective interleaved, or interlocking configuration with adjacent pads. Thus, according to some embodiments, the uncomfortable sensation of spread fingers, or splayed fingers is reduced or avoided.

Some embodiments of the systems 10, 100 are superior to simply adding shock-absorbing materials to the object being grasped, as they more directly diminish the flow of kinetic energy from the hitting implement to the elbow by targeting the specific tendons involved in the tendinosis. Moreover, the uniquely customizable options available using the systems 10, 100 and/or combinations thereof markedly diminish transmission of kinetic energy to the elbow without substantially affecting the user's ability to hold an object (e.g., a tennis racket). The systems 10, 100 can be customized for the individual user's tendon problems, generally do not require readjustment once placed on the finger(s), do not constrict the elbow, and do not constrict or abrade the finger(s). Though some exemplary features of the systems 10, 100 are described above, various additional or alternate features are contemplated.

Ranges mentioned herein include all ranges located within the prescribed range. As such, ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to about 7 also includes a limit of up to about 5, up to about 3, and up to about 4.5.

Various modifications, permutations, and additions can be made to the exemplary embodiments and aspects of the embodiments discussed without departing from the scope of the present invention. For example, while the embodiments describing a concave articular surface above refer to particular features, the scope of this invention also includes embodiments having different combinations of features and embodiments that do not include all of the features. Accordingly, the scope of the present invention is intended to embrace all such alternatives, modifications, permutations, and variations as fall within the scope of the claims, together with all equivalents thereof.

What is claimed is:

1. A method of preventing the development or exacerbation of tendinosis, the method comprising:

receiving a first ring of resilient material over a first digit of a hand of the user and a second ring of resilient material over a second digit of the hand of the user;

curling the first and second digits receiving first and second rings about an object to grasp the object with an increased circumference grip relative to a natural grip of the user;

automatically sliding the first and second rings to an interleaved configuration on the first and second digits by moving the grasped object with the hand, and automatically rotating the first and second rings about the first and second digits, respectively, by swinging the grasped object with the hand.

2. The method of claim 1, wherein the first and second rings of resilient material are received over proximal phalanges of the first and second digits, respectively.

3. The method of claim 2, wherein the first and second rings are configured such that the first and second rings do not slide beyond interphalangeal joints of the first and second digits during movement of the grasped object with the hand.

4. The method of claim 1, further comprising:
receiving a third ring of resilient material over a third digit of the hand of the user; and
inhibiting bending an interphalangeal joint of the third digit with the third ring of resilient material.

5. The method of claim 1, further comprising providing the first and second rings of a resilient material having a Shore Durometer 00 between approximately 55 and approximately 70.

6. A method of preventing the development or exacerbation of tendinosis, the method comprising:
receiving a first ring of resilient material over a first digit of a hand of the user and a second ring of resilient material over a second digit of the hand of the user;
curling the first and second digits receiving first and second rings about an object to grasp the object with an increased circumference grip relative to a natural grip of the user; and
automatically sliding the first and second rings to an interleaved configuration on the first and second digits by moving the grasped object with the hand,
wherein the grasped object is moved in an application that involves shock to the hand of the user, and
wherein the grasped object is moved during swinging of a tennis racket.

7. The method of claim 6, wherein the first and second rings of resilient material are received over proximal phalanges of the first and second digits, respectively.

8. The method of claim 7, wherein the first and second rings are configured such that the first and second rings do not slide beyond interphalangeal joints of the first and second digits during movement of the grasped object with the hand.

9. The method of claim 6, further comprising:
receiving a third ring of resilient material over a third digit of the hand of the user; and
inhibiting bending an interphalangeal joint of the third digit with the third ring of resilient material.

10. The method of claim 6, wherein the first and second rings comprise a resilient material having a Shore Durometer 00 between approximately 55 and approximately 70.

11. A method of preventing the development or exacerbation of tendinosis, the method comprising:
receiving a first ring of resilient material over a first digit of a hand of the user and a second ring of resilient material over a second digit of the hand of the user;
curling the first and second digits receiving first and second rings about an object to grasp the object with an increased circumference grip relative to a natural grip of the user;
automatically sliding the first and second rings to an interleaved configuration on the first and second digits by moving the grasped object with the hand;
receiving a third ring of resilient material over a third digit of the hand of the user;
curling the third digit receiving a third ring about the grasped object with the increased circumference grip relative to the natural grip of the user; and
automatically sliding the third ring on the third digit to an interleaved configuration with the first and second rings on the first and second digits by moving the grasped object with the hand.

12. The method of claim 11, wherein the first and second rings comprise a resilient material having a Shore Durometer 00 between approximately 55 and approximately 70.

* * * * *